US00PP20236P3

(12) United States Plant Patent
Sheehan

(10) Patent No.: US PP20,236 P3
(45) Date of Patent: Aug. 25, 2009

(54) ***GRAPEVINE* 'SHEEGENE-9'**

(50) Latin Name: *Grapevine*
Varietal Denomination: Sheegene-9

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 43 days.

(21) Appl. No.: 11/897,633

(22) Filed: Aug. 30, 2007

(65) Prior Publication Data

US 2009/0064383 P1 Mar. 5, 2009

(51) Int. Cl.
*A01H 5/00* (2006.01)

(52) U.S. Cl. ..... Plt./207

(58) Field of Classification Search ..... Plt./207
See application file for complete search history.

*Primary Examiner*—June Hwu
(74) *Attorney, Agent, or Firm*—Baker Manock & Jensen, PC; Eric C. Cole

(57) ABSTRACT

A new and distinct variety characterized by a green-colored, medium to large sized seedless grape that ripens during mid-July, approximately one week earlier than the Thompson Seedless Grape (unpatented) when grown in the San Joaquin Valley of Central California. The grapes of this new variety are produced on strong woody branches and are well adapted to commercial handling.

1 Drawing Sheet

Latin name of the genius and species of the plant claimed: The claimed plant relates to a new and distinct variety of *Vitis vinifera* to be known as 'Sheegene-9'.

Variety denomination: This invention relates to a new discovery and asexual reproduction of a new variety of *Vitis vinifera*. The new variety was first hybridized by Timothy P. Sheehan of Porterville, Calif. in late Spring 2000; first flowering occurred in May 2003. The pollen parent is Princess (unpatented) and the seed parent is Red Globe (U.S. Plant Pat. No. 4,787). The new variety was asexually propagated in the dormant season of 2003/2004, bud grafted on Harmony, virus-free rootstock, in a *Vitis vinifera* variety block located near Fowler, Calif. on the west side of Thompson Road, north of Adams Road. The green-colored seedless grapes produced by the new variety are medium to large in size and mature approximately one week before Thompson Seedless (unpatented). The new variety has been shown to maintain its distinguishing characteristics through asexual propagation.

The new variety is distinguished from its pollen parent, Princess (unpatented), in that the new variety produces green-colored seedless grapes, as compared to the white-colored seedless grapes produced by the pollen parent, Princess (unpatented). The new variety is distinguished from its seed parent, Red Globe (U.S. Plant Pat. No. 4,787), in that the new variety produces green-colored seedless grapes, as compared to its seed parent, Red Globe (U.S. Plant Pat. No. 4,787), that produces red-colored grapes.

BACKGROUND OF THE INVENTION

The present invention relates to a new and distinct variety of grape which will hereinafter be denominated as 'Sheegene-9' and more particularly as a grapevine which produces a green-colored seedless table grape that matures in mid July in the San Joaquin Valley of Central California. The new invention most closely resembles Thompson Seedless (unpatented) but it produces a medium to large size grape that is sweet, has very good flavor, and matures at least one week earlier.

SUMMARY OF THE INVENTION

The 'Sheegene-9' grapevine is characterized by producing a medium to large size green seedless grape with very good flavor that is mature for harvesting and shipment in mid July in the San Joaquin Valley of Central California. The new variety can be compared to Thompson Seedless (unpatented) but the grapes mature at least one week earlier, among other distinguishing characteristics.

BRIEF DESCRIPTION OF THE DRAWINGS

The accompanying drawing is a colored photograph of the grapes produced by the subject variety; several leaves are displayed as well as a typical section of the vine. Across the top of the color photograph to the left is a secondary growth clusters; and to the center and right is a small cane displaying several bifurcate tendrils and small leaves. Across the middle of the color photograph on the left is a mature grape cluster; and to the right are four berries (two longitudinally and two horizontally) displaying the flesh and shape. Below the four berries on the right is a shoot and tendrils and small leaves. Across the bottom of the color photograph to the left a mature leaf displaying the bottom surface; in the center is a secondary growth cluster; and to the right is a mature leaf displaying the top surface.

DETAILED BOTANICAL DESCRIPTION

Referring more to the horticultural description of the new and distinct variety of grapevine, the following has been observed under the ecological conditions prevailing at the origin vineyard that is located east of Fowler, Calif. in the San Joaquin Valley of Central California.

All major color descriptions are by reference to the Dictionary of Color by Maerz and Paul, First Edition, published in 1930. Common color names are also used in several instances.

VINE

Size: 5 feet (1.52 meters) in height, 31 to 36 inches (78.74 cm to 91.44 cm) in width.
Vigor: Very good.
Chilling requirements: Normal for grapevines in the San Joaquin Valley of Central California.
Figure: Wide cordons forming a "T" shaped figure.
Production capacity: Good.
Regularity of bearing: Regular.

TRUNK

Size: Medium to large; 8 inches (20.32 cm) in circumference, 32 inches (81.28 cm) above graft.
Surface texture: Rough and shaggy.
Color of bark: P1.7 H7 Cedar +.
Mature cane color: P1.7 H7 Tanagra Castilian Brown, Old Cedar.
Nodes: Five on canes, 13½ inches (34.29 cm) in length.
Length between nodes: 2½ to 5 inches (6.35 to 12.7 cm).
Lenticel number: None.
Lenticel size: 0.
Shoot contour: Drooping.
Tendril number: One at node.
Tendril length: 1⅜ to 3⅜ inches (4.45 to 8.57 cm).
Tendril form: Bifurcate.
Tendril texture: Firm to woody.
Bud shape: Triangular.
Bud size: 0.28 inches (7 mm) long by 0.28 inches (7 mm) wide.
Bud fruitfulness: Very good.
Bud break date: N/A.

BRANCHES

Size: Medium cordons; 31 inches (78.74 cm) from trunk on one side and approximately 36 inches (91.44 cm) on other side.
Surface texture: Slightly rough.
Color (one year older wood): P1.6 J10 Spanish Cedar.
Color (immature branches): P1.17 L6 Near Viridine gr.
Surface texture (immature branches): Smooth.

LEAVES

Size: Large.
Density: Dense.
Average length: 4½ to 7¼ inches (11.43 to 18.42 cm).
Average width: 6½ to 7¾ inches (13.97 to 22.23 cm).
Shape: Pentagonal.
Texture: Upper surface is smooth; Lower surface is glabrous.
Color (upward disposed surface): P1.23 J9 Polo Green.
Color (downward disposed surface): P1.20 L9 Eden Green.
Color (Leaf vein) P1.20 L5 Lettuce Green.
Marginal form: Generally slightly undulate.
Leaf vein (thickness): 0.12 inches (3 mm).
Leaf margin: Toothed.
Glandular characteristics: 0.
Petiole size: Large.
Petiole length: Average is 6.89 inches (17.5 cm).
Petiole thickness: Average is 0.20 inches (5 cm).
Petiole color: P1.17 L8 Neva Green.
Petiole sinus form: Reverse "U" shape.
Stem gland form: 0.
Stem gland position: 0.
Stem gland pattern: 0.
Stipules: Large 0.24 inches (6 mm).
Stipules color: P1.55 L8 Rubient.
Lobe average: Four.
Tooth size: Large; 0.63 to 0.94 inches (21 to 24 mm) in length, 0.24 to 0.35 inches (6 to 9 cm) in width.
Tooth number: Four large between lobes.
Tooth shape: Convex.

INFLORESCENCE

Size: Cluster is 4 to 9 inches (10.16 to 22.86 cm) in length.
Number borne per spur: Two to three.
Number borne per vine: 22 to 25.

FLOWERS

Flower buds (size): Small.
Flower buds (surface): Glabrous.
Flower buds (quantity): Moderate.
Date of bloom: Apr. 26, 2007.
Date of full bloom: May 5, 2007.
Size of bloom: 0.078 inch (2 mm).
Petal color: P1. 20 L9 - Eden gr.
Petal size: 0.078 inch (2 mm).
Pistil color: P1. 19 K10.
Amount of pollen: No data available.
Date of first visible berries: May 5, 2007.

FRUIT

Solids: 17.5° Brix.
Acids: 0.45.
Sugar/acid ratio: 37.2.
Juice pH: 3.86.
Seeds: 0.
Seed number: None.
Cap stem pedicel: Average 0.12 inches (10 mm).
Berry weight: 8.52 grams.
Juice color: P1.17 I6 Viridine Green.
Cluster size: Medium to large.
Cluster weight: 908.8 grams (32 oz.).
Cluster average length: 8½ inches (21.6 cm).
Cluster average width: 7 inches (7.78 cm).
Cluster form: Conical.
Stem: Generally variable; 7.2 cm.
Stem caliper: 5 mm.
Berry size: Large.
Berry size (average dimension along longitudinal axis): 0.92 to 1.02 inches (22 to 26 mm).
Berry size (average dimension along transverse axis): 0.79 o 0.92 inches (20 to 22 mm).
Berry shape: Ovate.
Berry number: Approximately 110 berries per bunch.

SKIN

Skin thickness: Medium.
Texture: Tough.
Ground color: P1.18 I7 Spring Green.
Pulp: Firm.

FLESH

Flesh color: P1.17 L7 Viridine Y.
Juice production: Very good.
Flavor: Very good.
Armoa: Mild.
Texture: Firm.
Ripening: Even.
Eating Quality: Very good.
Use: Fresh market.

Keeping quality: Very good.
Resistance to disease: None observed.
Harvesting and shipment: Mid July to September in the San Joaquin Valley of Central California.
Shipping and handling quality: Very good.
U.S.D.A Hardiness Zone: Zones 8 and 9.

Having thus described and illustrated our new variety of grapevine, we claim:

1. A new variety of grapevine to be known as 'Sheegene-9', substantially as illustrated and described, characterized principally by its production of green-colored, medium to large sized seedless grapes, that mature earlier in the season of ripening than does the Thompson Seedless Grape (unpatented) that it closely resembles.

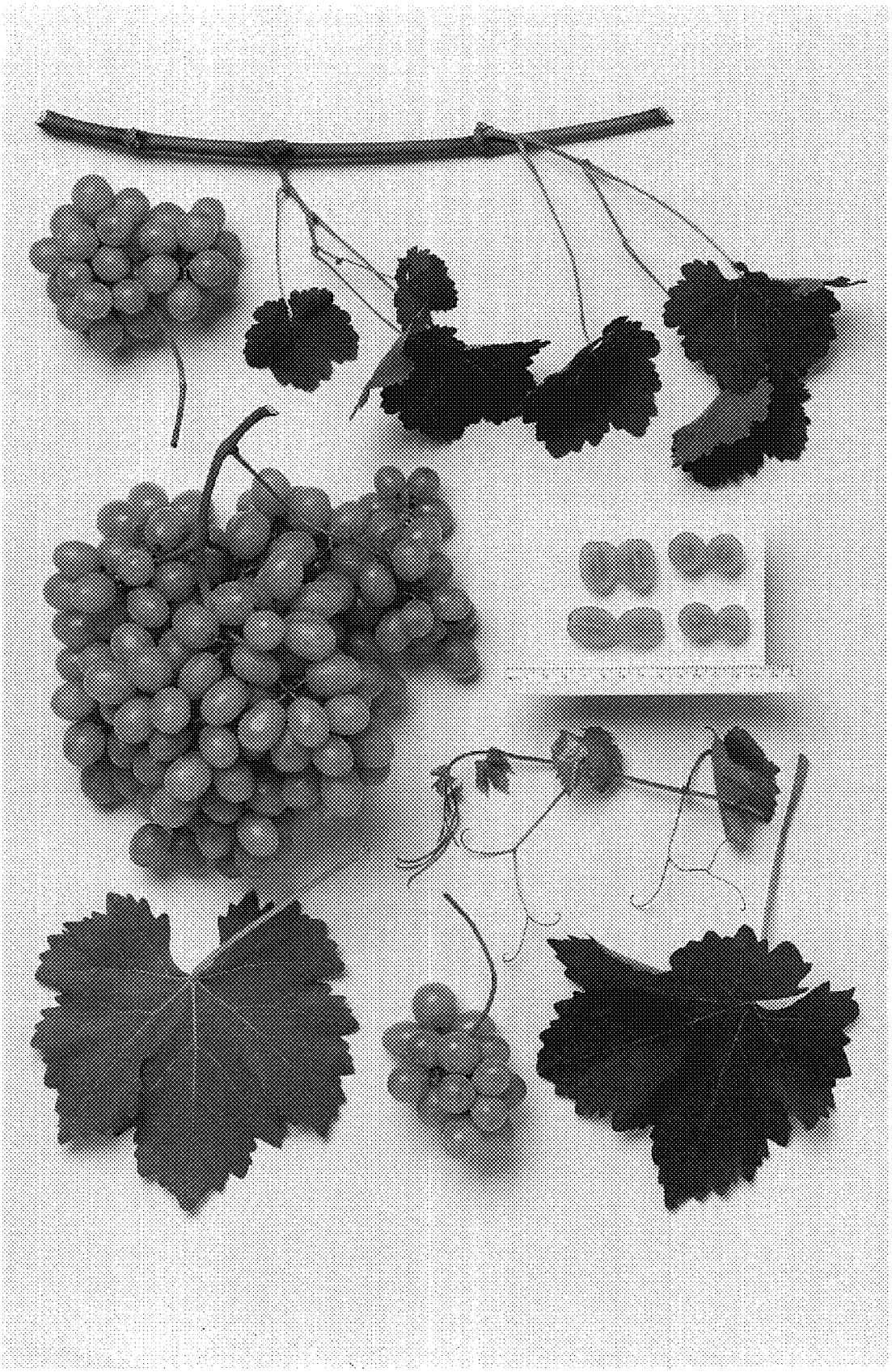

* * * * *